United States Patent
Polak et al.

(10) Patent No.: US 11,360,176 B2
(45) Date of Patent: Jun. 14, 2022

(54) RECONSTRUCTION OF MAGNETIC-RESONANCE DATASETS USING MACHINE LEARNING

(71) Applicants: Siemens Healthcare GmbH, Erlangen (DE); The General Hospital Corporation, Boston, MA (US)

(72) Inventors: Daniel Polak, Blankenbach (DE); Kawin Setsompop, Charlestown, MA (US)

(73) Assignees: Siemens Healthcare GmbH, Erlangen (DE); The General Hospital Corporation, Boston, MA (US)

( * ) Notice: Subject to any disclaimer, the term of this patent is extended or adjusted under 35 U.S.C. 154(b) by 87 days.

(21) Appl. No.: 16/778,800

(22) Filed: Jan. 31, 2020

(65) Prior Publication Data

US 2020/0249301 A1    Aug. 6, 2020

Related U.S. Application Data

(60) Provisional application No. 62/799,964, filed on Feb. 1, 2019.

(51) Int. Cl.
*G01V 3/00* (2006.01)
*G01R 33/56* (2006.01)
(Continued)

(52) U.S. Cl.
CPC ...... *G01R 33/5608* (2013.01); *G01R 33/5611* (2013.01); *G06N 20/00* (2019.01); *G16H 30/20* (2018.01)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

| | | | |
|---|---|---|---|
| 2006/0159346 A1* | 7/2006 | Lakare | G06T 7/0012 |
| | | | 382/206 |
| 2012/0033861 A1* | 2/2012 | Dai | G06K 9/6254 |
| | | | 382/128 |

(Continued)

OTHER PUBLICATIONS

Lustig, Michael et al., "Sparse MRI: The Application of Compressed Sensing for Rapid MR Imaging", in: Magnetic Resonance in Medicine, vol. 58, No. 6; pp. 1182-1195, 2007; XP007907974; ISSN: 0740-3194; DOI: 10.1002/MRM.21391; 2007.
(Continued)

*Primary Examiner* — Walter L Lindsay, Jr.
*Assistant Examiner* — Frederick Wenderoth
(74) *Attorney, Agent, or Firm* — Banner & Witcoff Ltd.

(57) ABSTRACT

A method includes determining an initial magnetic resonance imaging, MRI, dataset (201) in image domain based on an initial reconstruction of MRI measurement data obtained using an undersampling scheme (400); and determining patches (231-233) of the initial MRI dataset (201) in accordance with a patching scheme, the patching scheme depending on the undersampling scheme (400); and, for each one of the patches (231-233): applying a machine-learned algorithm to obtain a respective patch (231-233) of a reconstructed MRI dataset, the machine-learned algorithm depending on the undersampling scheme (400); and combining the patches (231-233) of the reconstructed MRI dataset.

19 Claims, 5 Drawing Sheets

Figure 1:
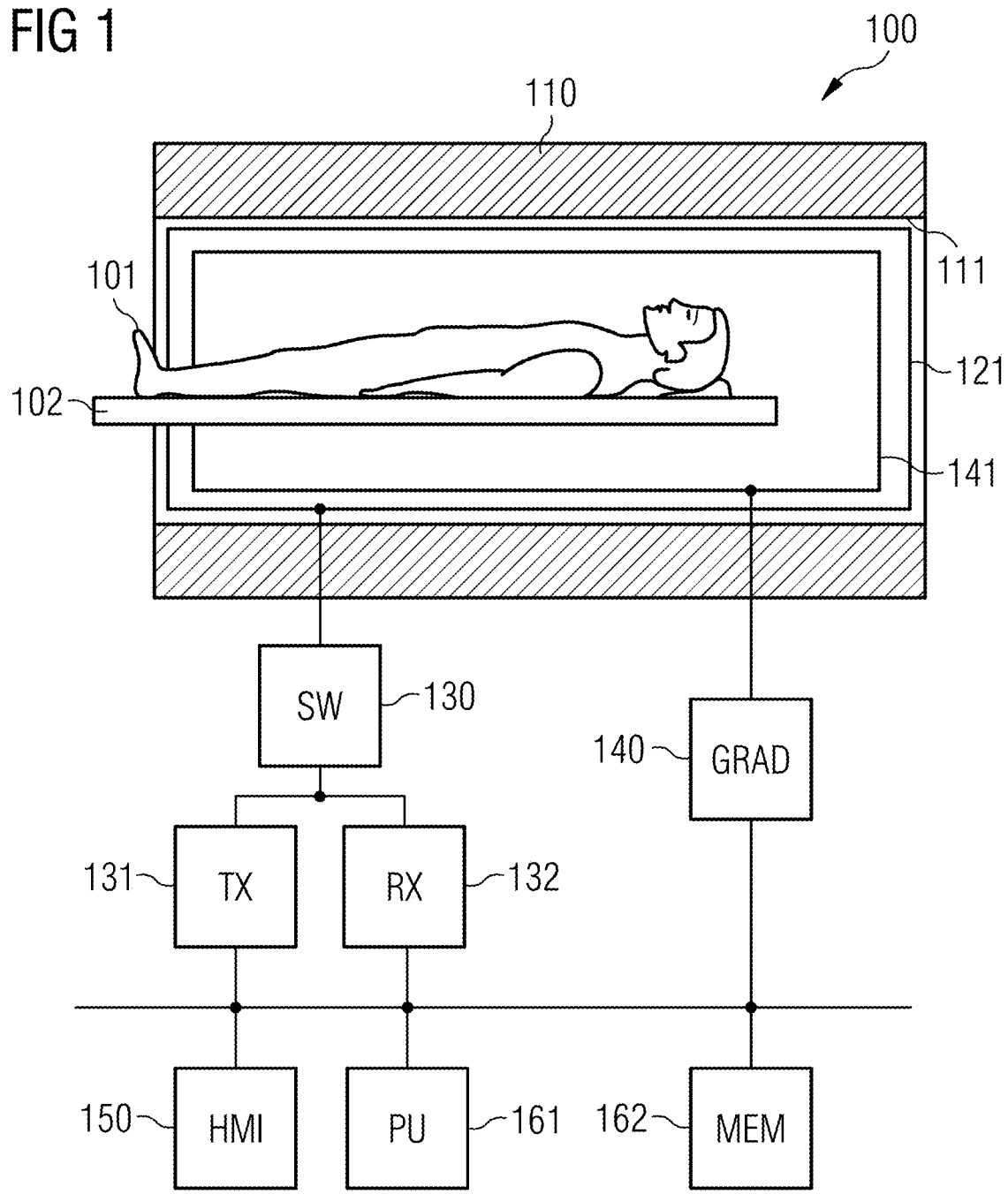

(51) Int. Cl.
*G16H 30/20* (2018.01)
*G06N 20/00* (2019.01)
*G01R 33/561* (2006.01)

(58) Field of Classification Search
USPC .......................................................... 324/309
See application file for complete search history.

(56) References Cited

U.S. PATENT DOCUMENTS

| | | | | |
|---|---|---|---|---|
| 2015/0355301 | A1* | 12/2015 | Zhang | G01R 33/5611 324/309 |
| 2016/0048963 | A1* | 2/2016 | Piestun | G06K 9/00 382/154 |
| 2018/0164395 | A1* | 6/2018 | Setsompop | G01R 33/5611 |
| 2019/0257905 | A1* | 8/2019 | Cheng | G01R 33/5611 |
| 2019/0285713 | A1 | 9/2019 | Polak et al. | |

OTHER PUBLICATIONS

Hammernik, Kerstin et al., "Learning a Variational Network for Reconstruction of Accelerated MRI Data", in: Magnetic Resonance in Medicine, vol. 79, pp. 3055-3071, 2018, DOI 10.1002/mrm. 26977.

Pruessmann, Klaas P. et al., "SENSE: Sensitivity Encoding for Fast MRI", Magnetic Resonance in Medicine, vol. 42, No. 5, pp. 952-962, Nov. 1999 (First published: Oct. 28, 1999) //https://doi.org/10.1002/(SICI)1522-2594 (199911)42:5<952::AID-MRM16>3.0.CO;2-S.

Breuer, Felix A. et al., "Controlled Aliasing in Volumetric Parallel Imaging (2D CAIPIRINHA)", Magnetic Resonance in Medicine, vol. 55, pp. 549â€"556, 2006 // DOI: DOI 10.1002/mrm.20787.

Griswold, Mark A. et al., "Generalized Autocalibrating Partially Parallel Acquisitions (GRAPPA)", Magnetic Resonance in Medicine, vol. 47, pp. 1202-1210, 2002 // DOI: 10.1002/mrm.10171.

Block et al., "Undersampled radial MRI with multiple coils Iterative", Magnetic Resonance in Medicine, vol. 57, No. 6; pp. 1086-1098, 2007.

Gong, Enhao et al., "Improving the PI+CS Reconstruction for Highly Undersampled Multi-contrast MRI using Local Deep Network", ISMRM abstract #5663, 2017.

Breuer, Felix A. et al., "Controlled Aliasing in Parallel Imaging Results in Higher Acceleration (CAIPIRINHA) for Multi-Slice Imaging", Magnetic Resonance in Medicine, vol. 53, No. 3, pp. 684-691, 2005 // DOI: 10.1002/mrm.20401.

J. Y. Cheng et al., "Highly Scalable Image Reconstruction using Deep Neural Networks with Bandpass Filtering", arXiv:1805.03300 [cs.CV], 2018.

Bilgic, Berkin et al., "Wave-CAIPI for Highly Accelerated 3D Imaging", Magnetic Resonance in Medicine, vol. 73, No. 6, pp. 2152-2162, 2015 // DOI: 10.1002/mrm.25347.

Zhu, Bo et al., "Image reconstruction by domain transform manifold learning", 2017, arXiv:1704.08841.

\* cited by examiner

FIG 3
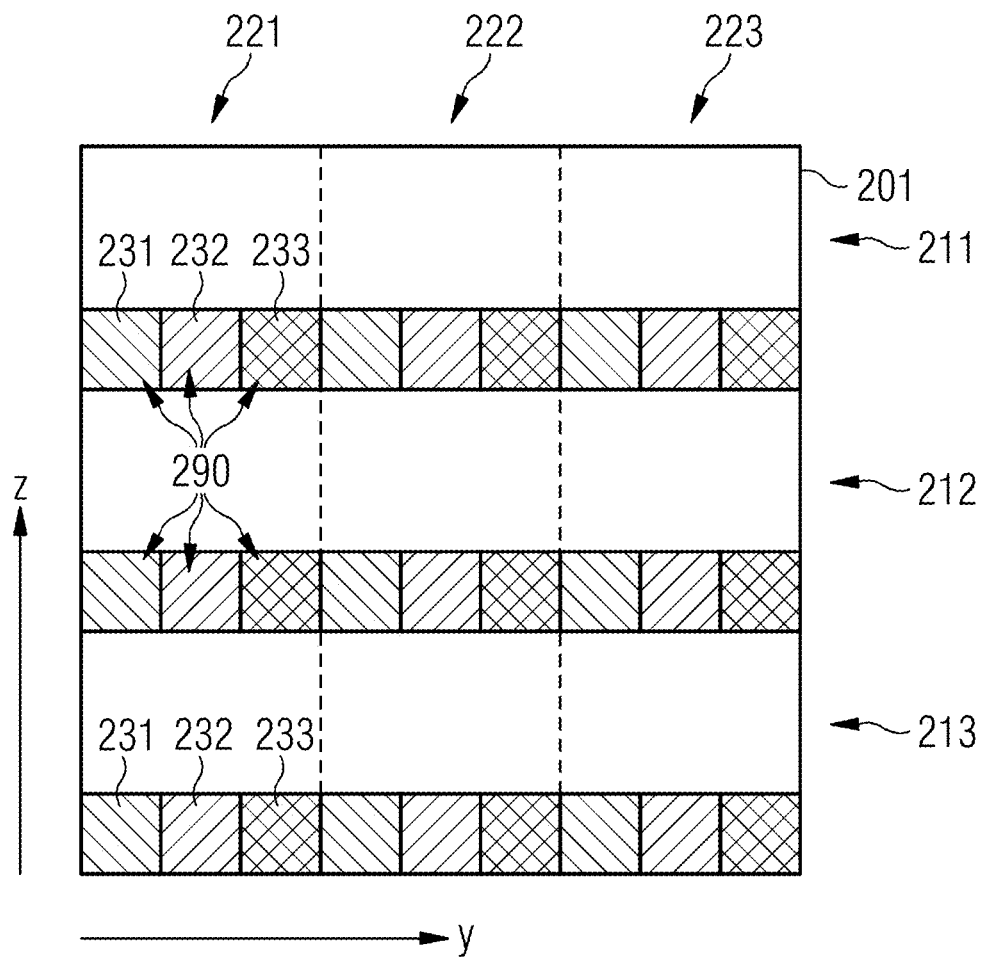
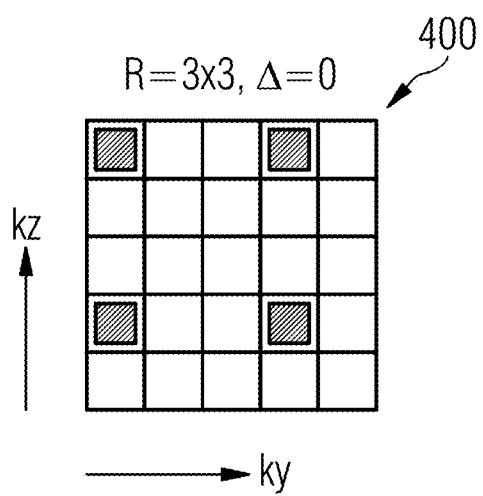

FIG 4
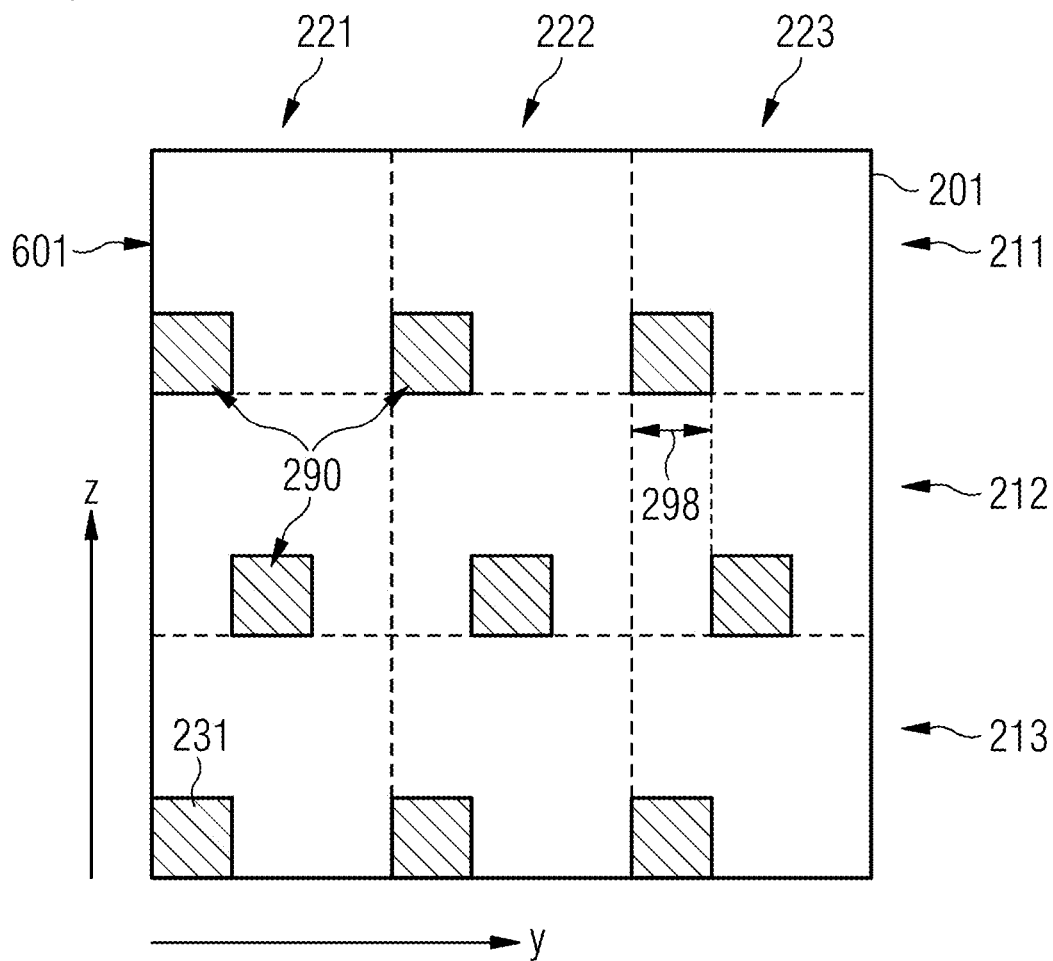
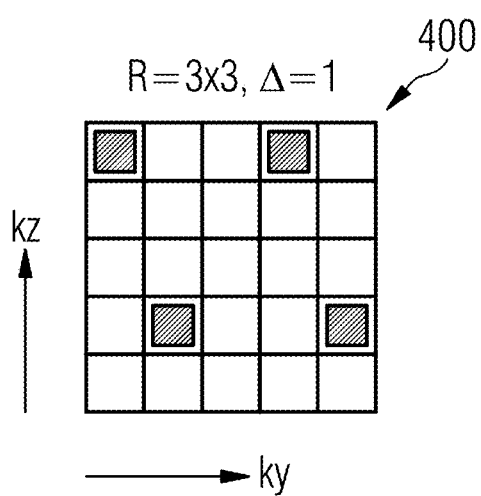

RECONSTRUCTION OF MAGNETIC-RESONANCE DATASETS USING MACHINE LEARNING

CROSS REFERENCE TO RELATED APPLICATIONS

This patent application claims priority to U.S. Provisional Patent Application No. 62/799,964, filed Feb. 1, 2019, which is incorporated herein by reference in its entirety.

BACKGROUND

Field

Various examples of the disclosure generally relate to magnetic-resonance imaging (MRI). Various examples specifically relate to machine-learned (ML) algorithms used to reconstruct MRI datasets.

Related Art

To accelerate MRI measurements, it is known to use undersampling schemes when acquiring raw MRI measurement datasets in K-space. Here, depending on the acceleration factor of the undersampling scheme, data samples are only taken for every second or third etc. K-space position. Then, a reconstruction of the undersampling MRI dataset can be implemented to obtain a reconstructed MRI dataset. This can be done, e.g., using conventional parallel acquisition techniques (PAT). Examples of PAT are described, e.g., in Pruessmann, Klaas P., et al. "SENSE: sensitivity encoding for fast MRI." Magnetic resonance in medicine 42.5 (1999): 952-962; and Griswold M A, Jakob P M, Heidemann R M, Mathias Nittka, Jellus V, Wang J, Kiefer B, Haase A. Generalized autocalibrating partially parallel acquisitions (GRAPPA). Magn Reson Med 2002; 47: 1202-1210; and Breuer, Felix A., et al. "Controlled aliasing in parallel imaging results in higher acceleration (CAIPIRINHA) for multi-slice imaging." *Magnetic resonance in medicine* 53.3 (2005): 684-691; and Bilgic, Berkin, et al. "Wave-CAIPI for highly accelerated 3D imaging." *Magnetic resonance in medicine* 73.6 (2015): 2152-2162.

The reconstructed MRI dataset can show artefacts and/or noise. For example, there may be a tendency towards artefacts and noise in scenarios in which an acceleration factor is too big. Thus, the image quality may suffer to some extent. To mitigate this drawback, techniques have been proposed that use an ML algorithm to refine the reconstructed MRI dataset, see, e.g., Hammernik, Kerstin, et al. "Learning a variational network for reconstruction of accelerated MRI data." *Magnetic resonance in medicine* 79.6 (2018): 3055-3071.

However, such techniques face certain restrictions and drawbacks. For example, volumetric 3-D MRI datasets can have a significant size. Sometimes, it is not possible to process the volumetric MRI datasets using the ML algorithm due to memory constraints of a working memory of the respective processing unit.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 schematically illustrates an MRI device according to an exemplary embodiment.

Figure 2:
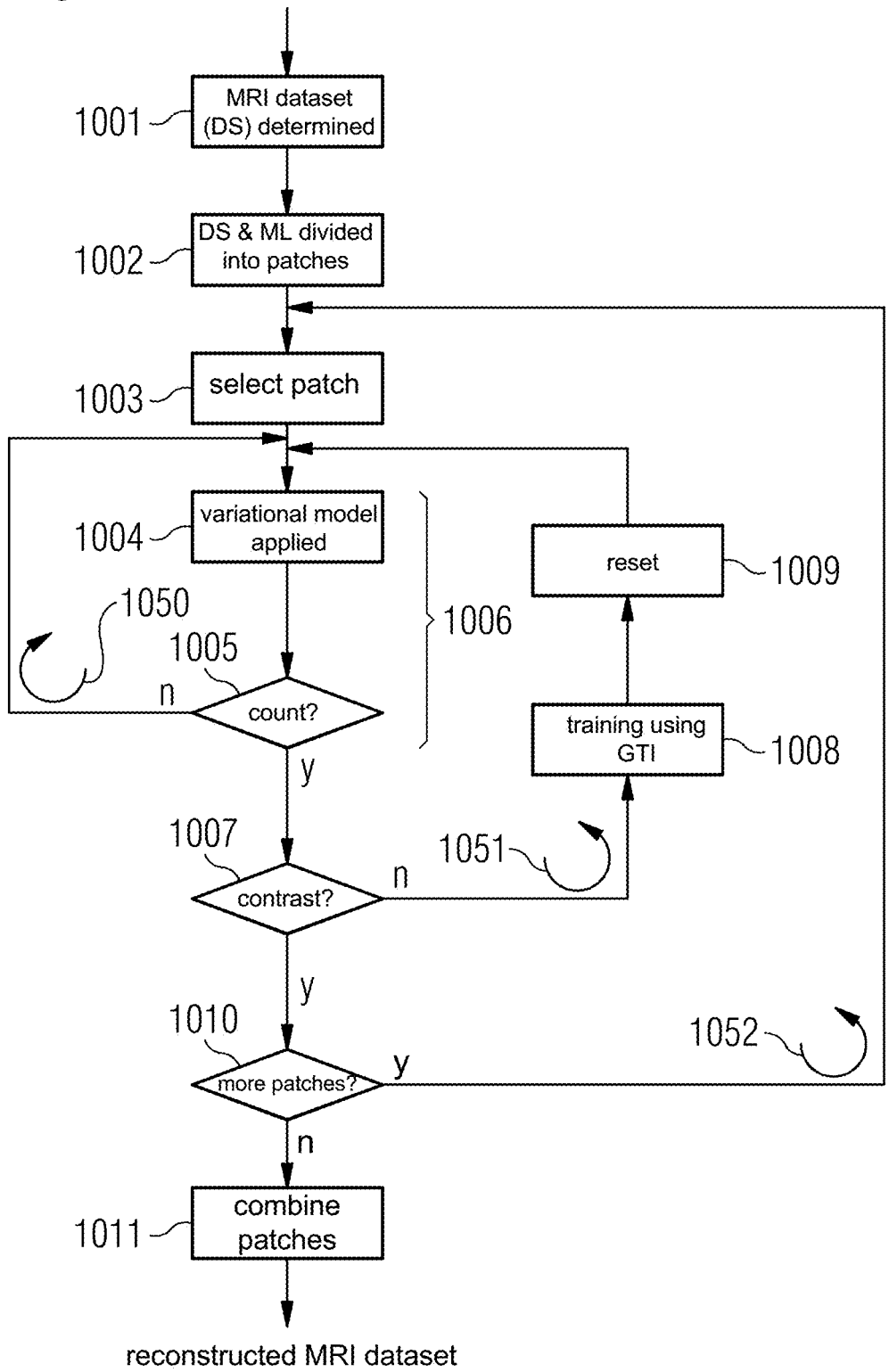

FIG. 2 is a flowchart of a method according to an exemplary embodiment.

FIG. 3 schematically illustrates patches determined for an initial MRI dataset in image domain according to an exemplary embodiment.

FIG. 4 schematically illustrates patches determined for an initial MRI dataset in image domain according to an exemplary embodiment.

Figure 5:
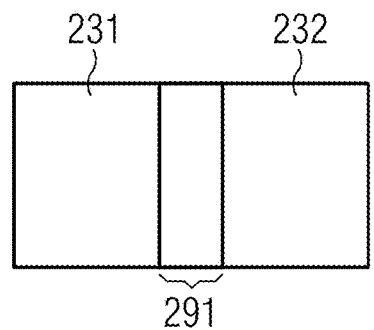

FIG. 5 schematically illustrates an overlap between adjacent patches according to an exemplary embodiment.

Figure 6:
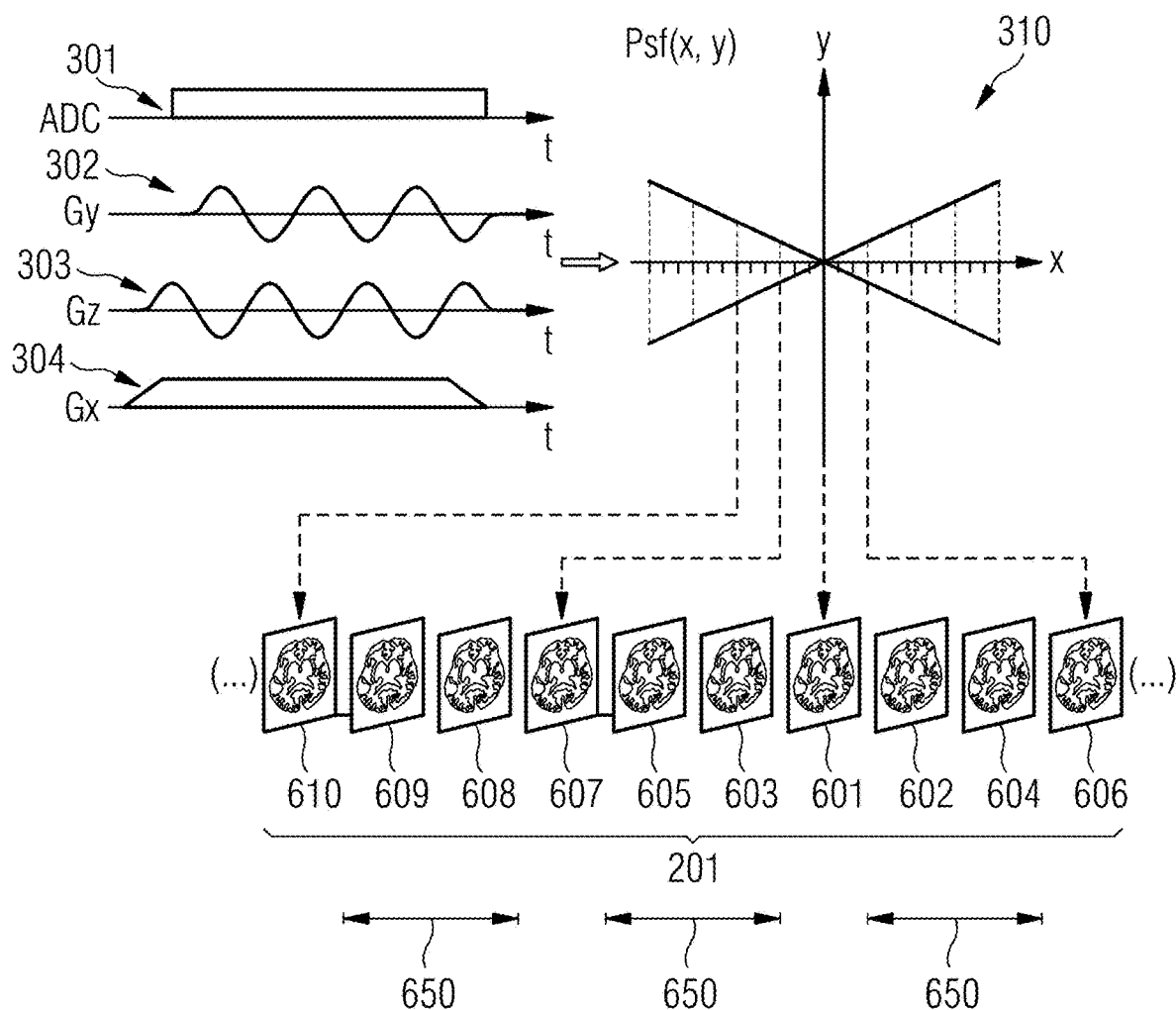

FIG. 6 schematically illustrates a point spread function associated with a K-space trajectory of an undersampling scheme according to an exemplary embodiment.

The exemplary embodiments of the present disclosure will be described with reference to the accompanying drawings. Elements, features and components that are identical, functionally identical and have the same effect are—insofar as is not stated otherwise—respectively provided with the same reference character.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to provide advanced techniques for reconstructing MRI datasets from undersampled MRI measurement datasets. For example, to provide techniques that overcome or mitigate at least some of the above-identified limitations and drawbacks.

In an exemplary embodiment, a method includes determining an initial MRI dataset in image domain. This is based on an initial reconstruction of MRI measurement data. The MRI measurement data is obtained for a field of view using an undersampling scheme. The method also includes determining patches of the initial MRI dataset in accordance with a patching scheme (sometimes also referred to as bricking scheme). The patching scheme depends on the undersampling scheme. Then, the method also includes, for each one of the patches: applying an ML algorithm, to obtain a respective patch of a reconstructed MRI dataset. The ML algorithm depends on the undersampling scheme. The method also includes combining the patches of the reconstructed MRI dataset.

In an exemplary embodiment, a computer program or a computer program product or a computer-readable storage medium is provided. The computer program or the computer program product or the computer-readable storage medium includes program code that can be executed by at least one processor. Executing the program code causes the at least one processor to perform a method. The method includes determining an initial MRI dataset in image domain. This is based on an initial reconstruction of MRI measurement data. The MRI measurement data is obtained for a field of view using an undersampling scheme. The method also includes determining patches of the initial MRI dataset in accordance with a patching scheme. The patching scheme depends on the undersampling scheme. Then, the method also includes, for each one of the patches: applying an ML algorithm, to obtain a respective patch of a reconstructed MRI dataset. The ML algorithm depends on the undersampling scheme. The method also includes combining the patches of the reconstructed MRI dataset.

A processor is configured to execute program code to perform a method. The method includes determining an initial MRI dataset in image domain. This is based on an initial reconstruction of MRI measurement data. The MRI measurement data is obtained for a field of view using an undersampling scheme. The method also includes determining patches of the initial MRI dataset in accordance with a patching scheme. The patching scheme depends on the undersampling scheme. Then, the method also includes, for each one of the patches: applying an ML algorithm, to obtain a respective patch of a reconstructed MRI dataset. The ML algorithm depends on the undersampling scheme. The method also includes combining the patches of the reconstructed MRI dataset.

For example, the MRI measurement data may be 3D volumetric measurement data.

For example, the ML algorithm may include one or more parameters that are determined using a training based on a ground truth MRI dataset.

It is to be understood that the features mentioned above and those yet to be explained below may be used not only in the respective combinations indicated, but also in other combinations or in isolation without departing from the scope of the disclosure.

Some examples of the present disclosure generally provide for a plurality of circuits or other electrical devices such as processors. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

Hereinafter, techniques of MRI described. MRI may be employed to obtain raw MRI measurement data of an magnetization of nuclear spins of a sample region of the patient. The sample region defines a field of view. The MRI measurement data is typically defined in K-space. Based on the MRI measurement data, MRI datasets in image domain can be determined.

According to various embodiments, the MRI measurement data can be obtained using an undersampling scheme. When acquiring MRI measurement data using an undersampling scheme, for certain K-space positions, raw data samples are not acquired and the missing information is reconstructed later on. A so-called acceleration factor R is indicative of the fraction of those K-space position along a K-space trajectory associated with the undersampling scheme for which no raw data samples are acquired. Larger (smaller) acceleration factors may result in a shorter (longer) scan times. For reconstruction of the missing information, respectively for determining a reconstructed MRI dataset, often a predetermined or calibrated sensitivity profile of multiple receiver coils of the RF receiver of the MRI device is used; thereby, aliasing effects resulting from the undersampling can be reduced to some extent. An analytic algorithm can be employed. Such techniques are sometimes referred to as a parallel acquisition techniques (PATs).

For example, the GRAPPA PAT (see Griswold M. A. et al.) linearly combines the undersampled MRI measurement data in K-space to estimate the missing samples in K-space; parameters of the combination are determined using auto-calibration signals (ACS) sampled with Nyquist rate, e.g., at K-space center. A respective kernel is defined.

For example, 2D-CAIPIRINHA PAT may shorten the scan time by reducing the number of phase encoding steps. This poses an intrinsic $\sqrt{\Box}$ penalty on the SNR where R is the acceleration factor (as for other PATs). Moreover, SNR is also affected by the encoding power of the PAT, also referred to as the geometry factor (g-factor). At high acceleration (approx. R>4), conventional 2D-CAIPIRINHA sometimes lacks sufficient encoding capability and localized g-factor hotspots arise, which cause severe noise amplification in the image and reduce the SNR.

According to examples, the reconstruction of an MRI dataset is facilitated using an ML algorithm. The ML algorithm can be applied to an initial MRI dataset. The initial MRI dataset can be reconstructed from undersampled MRI measurement data using a PAT, e.g., GRAPPA or CAIPIRINHA. Then, the ML algorithm can refine the reconstruction of the initial MRI dataset.

As a general rule, the ML algorithm employed in the various examples can include a trained neural network, e.g., a deep-learning network. The ML algorithm may include a variational model. The variational model can include (i) a regularization operator for filtering of the input MRI dataset (or a patch thereof) using convolutions and non-linear activations; and (ii) a forward-sampling operator (sometimes also referred to as data-consistency operator) for computation of an MRI forward model to assure agreement of the reconstructed MRI dataset with the MRI measurement data.

The ML algorithm may include multiple iterations of (i) and (ii), to iteratively refine the reconstructed MRI dataset; here, an appropriate optimization technique may be used.

By using the ML algorithm—e.g., by using a training to determine parameters of a variational model—, an increased image quality of the respective reconstructed MRI dataset can be provided. A reduced noise amplification and reduced image artefacts in comparison with the conventional PAT. The natural image appearance can be better preserved using ML algorithm, e.g., without causing significant blurring in comparison to techniques with hand-crafted regularization operators. Conventional techniques of determining the regularization operator are, e.g., total variation, see Block, Kai Tobias, Martin Uecker, and Jens Frahm. "Undersampled radial MRI with multiple coils. Iterative image reconstruction using a total variation constraint." *Magnetic Resonance in Medicine: An Official Journal of the International Society for Magnetic Resonance in Medicine* 57.6 (2007): 1086-1098; or L2 regularizer such as Thikinov; or wavelet transform, see Lustig, Michael, David Donoho, and John M. Pauly. "Sparse MRI: The application of compressed sensing for rapid MR imaging." *Magnetic Resonance in Medicine: An Official Journal of the International Society for Magnetic Resonance in Medicine* 58.6 (2007): 1182-1195). Such conventional compressed sensing techniques can be slow and can result in less natural looking images. Using the ML algorithm, faster image reconstruction can be achieved using a predefined number of iterations of the ML algorithm.

One or more parameters of the ML algorithm are determined using a training based on a ground-truth MRI dataset, before the reconstruction can be executed to provide a reconstructed MRI dataset. An offline end-to-end training is possible to obtain better results.

Typically, the training and/or execution of the ML algorithm is performed on a graphics processing unit (GPU): here, multiple parallel processing pipelines are provided which is used for efficient implementation of the training of the ML algorithm.

Often, processing unit such as a GPU have a limited size of the working memory. This can impose limitations on the application of a ML algorithm. For example, using conventional techniques of an ML algorithm including a variational model such as described by Hammernik, Kerstin, et al., reconstruction at high spatial resolution or volumetric 3-D MRI datasets may be limited. Further, MRI measurement data obtained using a large number of channels, i.e., receiver coils, can be problematic. For instance, techniques are known to use 32 or 64 channels in connection with head imaging or body arrays. Still further, acquisition techniques using a nonregular undersampling scheme such as random, Poisson disc, etc., cannot be used. Multi-echo and/or multi contrast imaging such as multiecho gradient echo or turbo-spin echo, MP2Rage, etc. may not be applied. According to various examples, an ML algorithm that can operate efficiently in view of memory constraints is provided.

According to various embodiments, a reconstruction procedure employs an ML algorithm. The reconstruction procedure applies the ML algorithm on size-limited patches of the field-of-view (FOV). Such approach using a patching scheme that defines the patches reduces the memory demands, because only a small fraction of the acquired MRI measurement data is processed one at a time. In other words: it is possible to apply the ML algorithm for each one of the patches, to obtain a respective patch of a reconstructed MRI dataset. The patches of the reconstructed MRI datasets can be finally combined to obtain the overall reconstructed MRI dataset.

Such an approach using a patching scheme can be of particular relevance for ML algorithms that use the (raw) MRI measurement data, such as variational models with integrated MRI forward model computation, see Hammernik, Kerstin, et al. More generally, the ML algorithm can depend on the undersampling scheme. To account for this dependency of the ML algorithm on the undersampling scheme, according to examples, the patching scheme can depend on the undersampling scheme, as well. For example, the patches can be determined in accordance with a K-space trajectory used for obtaining the samples of the MRI measurement data in K-space. Then, the patches are compatible with processing of the MRI measurement data by the ML algorithm. For example, by using the patching scheme in accordance with the undersampling scheme facilitates an efficient computation of the forward-sampling operator using only point-wise multiplications and summations; time-consuming Fourier transformations along the phase encoding direction/partition encoding direction (PAR; perpendicular to the phase encoding and readout direction) are not needed.

FIG. 1 illustrates aspects with respect to an MRI device 100 according to an exemplary embodiment. The MRI device 100 includes a magnet 110 which defines a bore 111. The magnet 110 can provide a DC magnetic field of one to six Tesla along its longitudinal axis. The DC magnetic field can align the magnetization of the patient 101 along the longitudinal axis. The patient 101 can be moved into the bore by means of a movable table 102.

In an exemplary embodiment, the MRI device 100 also includes a gradient system 140 for creating spatially-varying magnetic gradient fields (gradients) used for spatially encoding MRI data. Typically, the gradient system 140 includes at least three gradient coils 141 that are arranged orthogonal to each other and can be controlled individually. By applying gradient pulses to the gradient coils 141, it is possible to apply gradients along certain directions. The gradients can be used for slice selection (slice-selection gradients), frequency encoding (readout gradients), and phase encoding along one or more phase-encoding directions (phase-encoding gradients). Hereinafter, the slice-selection direction will be defined as being aligned along the Z-axis; the readout direction will be defined as being aligned with the X-axis; and a first phase-encoding direction as being aligned with the Y-axis. A second phase-encoding direction may be aligned with the Z-axis. The directions along which the various gradients are applied are not necessarily in parallel with the axes defined by the coils 141. Rather, it is possible that these directions are defined by a certain K-space trajectory which, in turn, can be defined by certain requirements of the respective MRI sequence and/or based on anatomic properties of the patient 101.

For preparation and/or excitation of the magnetization polarized/aligned with the DC magnetic field, RF pulses can be applied. For this, an RF coil assembly 121 is provided which is capable of applying an RF pulse such as an inversion pulse or an excitation pulse. While the inversion pulse generally inverts the direction of the longitudinal magnetization, excitation pulses can create transversal magnetization.

For creating such RF pulses, a RF transmitter 131 is connected via a RF switch 130 with the coil assembly 121. Via a RF receiver 132, it is possible to detect signals of the magnetization relaxing back into the relaxation position aligned with the DC magnetic field. In particular, it is possible to detect echoes; echoes may be formed by applying one or more RF pulses (spin echo) and/or by applying one or more gradients (gradient echo). The magnetization may inductively coupled with the coil assembly 121 for this purpose. The respectively acquired MRI measurement data can correspond to raw data in K-space; according to various examples, the MRI measurement data can be postprocessed in order to obtain images. Such postprocessing can include a Fourier Transform from K-space to image space. Such postprocessing can also include reconstruction to avoid aliasing where an undersampling scheme is used.

Generally, it would be possible to use separate coil assemblies for applying RF pulses on the one hand side and for acquiring MRI data on the other hand side (not shown in FIG. 1). For example, for applying RF pulses a comparably large body coil 121 can be used; while for acquiring MRI data a surface coil assembly including an array of comparably small coils could be used. For example, the surface coil assembly could include 32 individual RF coils and thereby facilitate PATs relying on spatially-offset coil sensitivities.

In an exemplary embodiment, the MRI device 100 further includes a human machine interface 150, e.g., a screen, a keyboard, a mouse, etc. By means of the human machine interface 150, a user input can be detected and output to the user can be implemented. For example, by means of the human machine interface 150, it is possible to set certain configuration parameters for the MRI sequences to be applied.

In an exemplary embodiment, the MRI device 100 further includes a processor 161. The processor 161 may include a GPU and/or a CPU. The processor 161 may implement various control functionality with respect to the operation of the MRI device 100, e.g., based on program code loaded from a memory 162. For example, the processor 161 could implement a sequence control for time-synchronized operation of the gradient system 140, the RF transmitter 131, and the RF receiver 132. The processor 161 can also be configured to implement a reconstruction procedure, i.e., implement postprocessing for reconstruction of an MRI dataset based on MRI measurement data. For example, the processor 161 could be configured to apply a PAT to obtain a reconstructed, initial MRI dataset and to apply a ML algorithm to obtain, based on the initial MRI dataset, a (refined) reconstructed MRI dataset. Details with a reconstruction procedure that can be executed by the processor 161 based on program code loaded from the memory 162 is illustrated in connection with FIG. 2.

FIG. 2 is a flowchart of a method according to exemplary embodiments. For example, the method according to FIG. 2 may be executed by the processor 161 of the MRI device 100 according to the example of FIG. 1. It would also be possible that the method is executed by a separate compute unit, e.g., at a server backend. FIG. 2 illustrates aspects with respect to an example reconstruction procedure.

Initially, at block 1001, an initial MRI dataset is determined in image domain.

Block 1001 may include acquisition of undersampled MRI measurement data. An MRI protocol defining RF pulses, gradient pulses, readout, etc. can be used. The MRI measurement data may be obtained for a FOV using an undersampling scheme. The undersampling scheme may be a regular cartesian sampling scheme.

In block 1001, initial reconstruction of the MRI measurement data using a PAT can be employed. For example, CAIPIRINHA or Wave-CAIPI could be employed to obtain the initial MRI dataset. Such techniques typically include filling non-acquired samples with zeros and performing a Fourier transformation of the K-space MRI measurement data. Then, the PAT analytical reconstruction algorithm based on the ACS data can be employed. This typically includes computing coil sensitivity maps from internal/external ACS data; if a wave-CAIPI-type PAT is used, the point-spread-function (PSF) can be calculated. The PSF is generally associated with the K-space trajectory of the undersampling scheme (spirals in the case of Wave-CAIPI).

The initial MRI dataset may have residual artefacts. To reduce these residual artefacts, next, at block 1002, patches of the initial MRI dataset of block 1001 are determined. This is in accordance with a patching scheme. The patching scheme depends on the undersampling scheme of block 1001. Details with respect to the patches determined based on the patching scheme are explained in connection with FIG. 3, FIG. 4, FIG. 5, and FIG. 6

FIG. 3 schematically illustrates the initial MRI dataset 201 in image domain according to an exemplary embodiment. The initial MRI dataset 201 in FIG. 3 is determined based on the MRI measurement data that is obtained using a regular R=2×2 undersampling scheme 400 of SENSE-type (i.e., cartesian K-space trajectory with a shift factor $\Delta=0$, see F. A. Breuer et al.; the undersampling scheme 400 is illustrated in the inset of FIG. 3).

FIG. 3 illustrates aspects with respect to patches 231-233 that are defined in accordance with a patching scheme, according to an exemplary embodiment. The patching scheme defines the number, arrangement, overlap, etc. of the patches 231-233. Each patch 231-233 includes a subfraction of all voxels of the initial MRI dataset 201.

In the example of FIG. 3, patches 231-233 are determined for the initial MRI dataset 201 (in fact, a total of 9 patches are determined, however, in FIG. 3, for sake of simplicity only 3 patches are illustrated with the different fillings). As illustrated in FIG. 3, each patch 231-233 includes voxels of multiple sub-regions 290 of the initial MRI dataset. The sub-regions 290 are offset from each other.

The size of the sub-regions 290 (and, hence, also their count and the count of voxels per patch 231-233) could be predefined. It would also be possible to determine the size of the sub-regions 290 depending on a size of the memory 162 available to hold the respective data when applying the ML algorithm.

The sub-regions 290 are selected in accordance with the undersampling scheme 400. In FIG. 3, a R=3×3 undersampling scheme 400 is used. Hence, the overall initial MRI dataset 201 is divided into 3×3 groups 209 of collapsing voxels. Then, each group 209 is divided into a number of sub-regions 290 associated with the patches 231-233. In other words and more generally, the sub-regions 290 are interleaved in accordance with the acceleration factor of the undersampling scheme 400.

Also, the sub-regions 290 of each one of the patches 231-233 are shifted with respect to each other and depending on the CAIPIRINHA shifting factor of the undersampling scheme 400 ($\Delta=0$ in FIG. 3, hence there is no shift; but FIG. 4 schematically illustrates the shift 298 of the sub-regions 290 of the patch 231 for a R=3$\Delta$3, $\Delta=1$ CAIPIRINHA-encoding undersampling scheme 400). The shift 298 is relatively defined between the patches 231-233 of each group 209.

While in FIG. 3 and FIG. 4, no overlap between adjacent patches 231-233 is illustrated, in some examples it would be possible that there is an overlap 291 defined between the patches (cf. FIG. 5). Provisioning the overlap 291 helps to further increase the image quality.

Then, each patch 231-233 is populated with the voxels of the initial MRI dataset 201 that are within the sub-regions 290 of a given patch 231-233. Note that FIG. 3 and FIG. 4 illustrate a slice defined perpendicular to the readout direction (x-direction) and by the phase-encoding directions (y- and z-directions). In some examples, all slices can be treated individually. In some examples it can be desirable to extend the patches 231-233 along the readout direction—this is generally optional. For example, this may help to shorten the processing time. Also, extending the patches 231-233 along the readout direction, i.e., along all 3-D directions, allows to perform 3-D filtering instead of 2-D filtering (e.g., in connection with a forward-sampling operator). This may help to improve the image quality. Here, the dimension along the readout direction can be smaller if compared to the dimension of the patches 231-233 along the phase-encoding directions. Extension of the patches 231-233 along the readout direction can also be helpful where there is a coupling of readout and phase-encoding, e.g., as for wave-CAIPI encoding. If a wave-CAIPI-encoding of the undersampling scheme 400 is used, the readout direction and the phase encoding directions are coupled. Thus, each patch 231-233 should be generally populated with all samples along the readout direction. This can strongly increase the data volume. To mitigate this, according to examples described herein, it is possible to take advantage of sparse property of Wave-CAIPI along the readout. This is illustrated in FIG. 6: In FIG. 6, the readout duration 301, the sinusoidal gradients along the phase-encoding directions 302, 303, and the readout gradient along the readout direction 304 are illustrated. The corresponding PSF 310 in image space is also illustrated. Then, instead of populating the patches with the voxels taken during the entire sampling duration 301, it is possible to use only every n-th voxel, where n corresponds to the number of sinusoidal cycles of the wave oscillation along the phase encoding directions 302, 303. Generally speaking, it would be possible to populate the patches 231-233 with voxels of the initial MRI dataset 201 in the readout direction 304, in accordance with the PSF 310. Specifically, the sparsity of the PSF 310 can be taken into account when populating the patches. As illustrated in FIG. 6, the Wave PSF 310 allows de-coupling of the readout voxels. This is particularly helpful as the forward-sampling operator does not require the entire readout (i.e., data of all slices 601-610), but only a subset of slices 601, 606, 607, 610 (illustrated by the arrows in FIG. 6). This helps to retain tractable memory demands. However, the image quality for 3-D datasets improves when the filtering operations are performed on 3-D patches being populated from more than a single slice 601-610 (and not just a single 2-D slice 601-640). In a No-Wave CAIPI acquisition, one has free choice of the patch dimension along the readout direction kx, as there is no coupling along this dimension. In Wave CAIPI, one has to choose the voxels in agreement with the coupling pattern (populate voxels from very n-th slice 601, 606, 607, 610, where n=number of cycles, other slices can be neglected 602-605, 608-609; in FIG. 6, n=3). However, the voxels used for populating the patches in slices 601, 606, 607, 610 are not neighboring (there are gaps 650 in-between). Then, as such, 3-D filtering cannot be applied. To mitigate this issue, one can include the voxels in the slices 602-605, 608-609 arranged in the gaps 650 in the filtering step of the regularization operator, but discard them in the remaining aspects of the forward-sampling operator computation. Hence, the input 3-D MRI dataset 201 could include a larger portion of the voxels in slices 601-610 along the readout direction, but the heavy lifting for storing the coil sensitivity, PSF and raw data as well as the computation of the forward-sampling operator may be restricted to voxels in the coupled slices 601, 606-607, 610.

Thus, in short, wherein the patches 231-233 can be initially populated with the voxels from a first set of slices 601-610 of the initial MRI dataset 201 (e.g., all slices). Then, the regularization operator can be applied to the thus-populated patches. Then, upon applying the regularization operator, only voxels from a second set of slices 601, 606-607, 610 are retained in the patches 231-233. Thus, some voxels can be discarded from the patches 231-233. Such thinning-out can be in accordance with the PSF 310 as discussed above. Upon (only) retaining the voxels from the second set of slices 601, 606-607, 610, the forward-sampling operator is applied.

This allows us to take advantage of both filtering along 3-D and efficient forward operator computation.

Thus, patching schemes as described in connection with FIG. 3, FIG. 4, FIG. 5, and FIG. 6 are helpful to efficiently implement the ML algorithm as part of the reconstruction procedure. This is particularly true where the ML algorithm depends on the undersampling scheme 400. Namely, it is then possible to efficiently implement the computational operations on a parallelized compute platform such as a GPU. Next, details with the respect to the ML algorithm are explained.

Now referring again to FIG. 2, in block 1002, not only the initial MRI dataset 201, but also other inputs of the ML algorithm are divided into patches according to the patching scheme. Depending on the ML algorithm, this may include the coil-sensitivity maps, a ground truth image (for training of the ML algorithm), and the MRI measurement data. This may also include the PSF 310, e.g., if Wave-CAIPI encoding is used for the undersampling scheme 400 (cf. FIG. 6). Next, at block 1003 a current patch is selected. Then, at block 1006, the ML algorithm is applied for the currently selected patch. The ML algorithm includes application of a variational model at 1004. The variational model has parameters that are determined based on a training using the ground-truth dataset. An offline training may be used such that these parameters are effectively predefined.

The ML algorithm includes multiple iterations 1050; at 1005, it is checked whether a further iteration 1050 is required. Abort criteria at block 1005 may be a threshold count of iterations, a change of the results from iteration to iteration 1050, etc.

Inputs of the variational model at 1004 are the currently selected patch of the coil sensitivity maps and the currently selected patch of the raw MRI measurement data (i.e., respective sub-regions). Further optional inputs include the PSF and information regarding the undersampling pattern, e.g., a K-space trajectory, ASF data, etc. As such, the ML algorithm depends on the undersampling scheme 400 in that it uses the un-reconstructed, raw MRI measurement data— i.e., the respective patch of the raw MRI measurement data. The respective patch is obtained from block 1002.

A further input of the parameterized network at 1004 is—at the first iteration 1050—the currently selected patch of the initial MRI dataset (i.e., respective sub-regions 290, cf. FIG. 3 and FIG. 4) from block 1001.

The output of block 1004 is the current patch of the reconstructed MRI dataset. The current patch of the reconstructed MRI dataset corresponds to a revised version of the current patch of the initial MRI dataset.

At the subsequent, second iteration 1050, the output of block 1004 of the previous, first iteration 1050 is used as an input (instead of the initial MRI dataset 201). Thereby, the respective patch of the reconstructed MRI dataset is iteratively refined from iteration 1050 to iteration 1050.

In an exemplary embodiment, the ML algorithm—or, more specifically, the variational model of block 1004—can include a regularization operator that is applied on the respective patch 231-233 of the input reconstructed MRI dataset of the respective iteration 1050. The regularization operator can include a filter e.g., a non-linear filter and/or a convolutional filter (e.g., a directed convolutional filter). 2-D or even 3-D convolutions may be applied. Non-linear activations may be applied. These filters may be applied in the phase-encoding plane. There may be no differentiation along the read-out directions.

In an exemplary embodiment, the ML algorithm—or, more specifically, the network of block 1004—could also include a forward-sampling operator. The forward-sampling operator can be associated with the coil sensitivity maps, the raw MRI measurement data and a Fourier transformation thereof, or—more generally—the undersampling scheme 400. For example, the forward-sampling operator may include a point-wise multiplication of the respective patch 231-233 of the input reconstructed MRI dataset with the respective patch of the coil sensitivity, and a summation over the collapsing voxel groups, possibly with the Wave PSF and FFT. The forward-sampling operator may include a subtraction of the raw MRI measurement data therefrom and application of the Hermitian of the forward model, which includes point-wise multiplication of the respective patch of the conjugate coil sensitivity map and a summation over the channels. Additionally, the data agreement can be weighted using a regularization parameter.

In an exemplary embodiment, at optional block 1007, an end-to-end training can be selectively triggered. At block 1007, it is checked whether the contrast of the patch 231-233 of the reconstructed MRI dataset obtained from the final iteration 1050 conforms well with the respective patch of the ground-truth MRI dataset. The comparison between the ground truth MRI dataset and current stage of the ML output is performed, e.g., by computing the L2 norm of the difference between the two datasets (sometimes called loss function) A respective comparison can be implemented between the patch of the reconstructed MRI dataset and the respective further patch of the ground-truth MRI dataset. If there is a significant discrepancy (e.g., determined using a distance metric and a threshold comparison) and/or if a certain threshold number of iterations 1051 has not yet been reached, a training of the network of block 1008 is triggered based on the ground-truth image. The parameters of the network are adjusted. Then, after a reset at block 1009, the ML algorithm is re-applied in multiple iterations 1050 of block 1006. The end-to-end training defines an outer loop of iterations 1051. Note that the training is implemented on patch-level which helps to meet memory restrictions.

At block 1010 it is checked whether a further patch needs to be processed. If yes, then at block 1003 the next patch is selected, and the ML algorithm is re-executed at a further outer-loop iteration 1052 of block 1006.

Once all patches have been processed, at block 1011, the patches of the reconstructed MRI dataset obtained from the various outer loop iterations 1052 are combined. The final reconstructed MRI dataset is obtained.

Summarizing, techniques have been described that expand use of ML algorithms for reconstruction of undersampled MRI measurement data to volumetric 3-D MRI. A regular cartesian undersampling scheme can be used. Optionally, CAIPIRINHA or Wave-CAIPI encoding of the K-space samples can be used.

According to various embodiments, the reconstruction procedure operates on patches of image space. Since a regular undersampling scheme can be used, the reconstruction procedure is compatible with many scanning protocols employed today at MRI devices.

By using Wave-CAIPIRINHA sampling, first, the quality of the initial reconstructed MRI dataset can be increased; second it is possible to make use of the sparse coupling pattern of the PSF defined by the Wave-CAIPI K-space trajectory: patches are not required to be fully populated with voxels along the readout direction. This reduces the processed data amount by at least an order of magnitude, which helps enable the DL reconstruction also on lower-end MRI systems with moderate computation hardware.

Although the disclosure has been shown and described with respect to exemplary embodiments, equivalents and modifications will occur to others skilled in the art upon the reading and understanding of the specification. The present disclosure includes all such equivalents and modifications and is limited only by the scope of the appended claims.

For instance, while above various examples have been explained in connection with a processor executing a reconstruction procedure being part of an MRI device, it would also be possible that a separate processor is used, e.g., at a server backend.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method, comprising:
    determining an initial magnetic resonance imaging (MRI) dataset in an image domain based on an initial reconstruction of MRI measurement data obtained using an undersampling scheme;
    determining patches of the initial MRI dataset in accordance with a patching scheme, the patching scheme depending on the undersampling scheme;
    for each one of the patches, applying a machine-learned algorithm to obtain a respective patch of a reconstructed MRI dataset, the machine-learned algorithm depending on the undersampling scheme; and
    combining the patches of the reconstructed MRI dataset.

2. A system comprising:
    a memory that stores program code; and
    a processor configured to load the program code from the memory and execute the program code to:
        determine an initial magnetic resonance imaging (MRI) dataset in an image domain based on an initial reconstruction of MRI measurement data obtained using an undersampling scheme;
        determine patches of the initial MRI dataset in accordance with a patching scheme, the patching scheme depending on the undersampling scheme;
        for each one of the patches, apply a machine-learned algorithm to obtain a respective patch of a reconstructed MRI dataset, the machine-learned algorithm depending on the undersampling scheme; and
        combine the patches of the reconstructed MRI dataset.

3. The method of claim 1, wherein each patch comprises voxels in multiple sub-regions of the initial MRI dataset, the sub-regions being selected in accordance with the undersampling scheme and being offset from each other.

4. The method of claim 3, wherein the sub-regions of two patches of the initial MRI dataset are interleaved in accordance with an acceleration factor of the undersampling scheme.

5. The method of claim 3, wherein the sub-regions of a given patch of the initial MRI dataset are shifted with respect to each other in accordance with a shifting factor of the undersampling scheme.

6. The method of claim 1, wherein the patching scheme defines overlaps between adjacent ones of the patches.

7. The method of claim 1, further comprising: populating the patches with voxels of the initial MRI dataset along a readout direction.

8. The method of claim 7, wherein the patches are populated with voxels from slices of the initial MRI dataset selected in accordance with a point spread function associated with the undersampling scheme.

9. The method of claim 8, wherein the patches are populated with voxels along the readout direction based on a sparsity of the point spread function.

10. The method of claim 1, wherein the undersampling scheme is associated with a controlled aliasing in parallel imaging results in higher acceleration (CAIPIRINHA) encoding or a Wave-controlled aliasing in parallel imaging (Wave-CAIPI) encoding.

11. The method of claim 1, wherein the machine-learned algorithm is applied using a processor coupled to a memory, wherein the method further comprises: determining a size of the patches based on a size of the memory.

12. The method of claim 1, wherein the machine-learned algorithm comprises multiple iterations of a variational model, the variational model including a forward-sampling operator being applied on the respective patch of the reconstructed MRI dataset of a given iteration and the respective patch, the forward sampling operator being associated with coil sensitivity maps, Fourier transform, and the undersampling scheme.

13. The method of claim 1, wherein the machine-learned algorithm comprises multiple iterations of a variational model, the variational model including a regularization operator being applied on the respective patch of the reconstructed MRI dataset of a given iteration, the regularization operator being associated with at least one of a convolutional filter and a non-linear filter.

14. The method of claim 7, wherein:
    the machine-learned algorithm comprises multiple iterations of a variational model, the variational model including: a forward-sampling operator being applied on the respective patch of the reconstructed MRI dataset of a given iteration and the respective patch, and a regularization operator being applied on the respective patch of the reconstructed MRI dataset of a given iteration,
    the patches are populated with the voxels from a first set of slices of the initial MRI dataset,
    the regularization operator is applied to the patches upon populating the patches,
    upon applying the regularization operator, voxels from a second set of slices are retained in the patches, and
    upon retaining the voxels from the second set of slices, the forward-sampling operator is applied.

15. The method of claim 1, wherein the machine-learned algorithm comprises parameters that are determined based on training using a ground-truth MRI dataset.

16. The method of claim 15, further comprising:
    obtaining an MRI ground truth dataset;
    determining patches of the MRI ground truth dataset in accordance with the patching scheme; and
    for at least one patch of the MRI ground truth dataset, performing a training of the machine-learned algorithm based on a comparison between the respective at least one patch of the reconstructed MRI dataset and the respective at least one patch of the MRI ground truth dataset.

17. A non-transitory computer-readable storage medium with an executable program stored thereon, that when executed, instructs a processor to perform the method of claim 1.

18. A computer program product having a computer program which is directly loadable into a memory of a controller of the magnetic resonance imaging system, when executed by the controller, causes the magnetic resonance system to perform the method as claimed in claim 1.

19. The system of claim 2, further comprising an MRI scanner that is configured to perform a magnetic resonance imaging on a patient to obtain the MRI measurement data.

* * * * *